United States Patent [19]

Thomas

[11] Patent Number: 5,728,147
[45] Date of Patent: Mar. 17, 1998

[54] BODY PAD

[76] Inventor: James L. Thomas, 2007 Victoria Rd., Mendota Heights, Minn. 55118

[21] Appl. No.: 908,435

[22] Filed: Jun. 30, 1992

Related U.S. Application Data

[63] Continuation of Ser. No. 702,502, May 20, 1991, abandoned.

[51] Int. Cl.$^6$ ........................................ A61F 7/08
[52] U.S. Cl. .................................. 607/112; 5/655.9
[58] Field of Search ............................. 128/399–403, 128/390; 802/2; 2/81, 82; 5/498, 500, 481, 483, 502; 126/204

[56] References Cited

U.S. PATENT DOCUMENTS

| | | | |
|---|---|---|---|
| 2,909,176 | 10/1959 | Asho | 128/402 |
| 2,911,974 | 11/1959 | Spemce | 128/402 |
| 3,092,110 | 6/1963 | Duensihp | 128/402 |
| 3,259,925 | 7/1966 | Tilles | 5/481 |
| 3,518,995 | 7/1970 | Claff | 128/379 |
| 3,815,610 | 6/1974 | Winther | 128/380 |
| 4,081,150 | 3/1978 | Tyson | 128/402 |
| 4,274,158 | 6/1981 | Pogorsti | 2/82 |
| 4,326,310 | 4/1982 | Frankenberg | 5/483 |
| 4,470,417 | 9/1984 | Gruben | 128/402 |
| 4,556,055 | 12/1985 | Bonner | 128/82.1 |
| 4,583,247 | 4/1986 | Fingerhut | 5/498 |
| 4,585,003 | 4/1986 | Meistrell | 128/402 |
| 4,587,962 | 5/1986 | Green | 128/80 H |
| 4,596,250 | 6/1986 | Beisamg, III et al. | 128/402 |
| 4,604,987 | 8/1986 | Kelther | 126/204 |
| 4,645,498 | 2/1987 | Kosam | 128/403 |
| 4,676,247 | 6/1987 | Van Cleve | 128/402 |
| 4,924,543 | 5/1990 | Hall et al. | 5/502 |
| 4,961,230 | 10/1990 | Limb et al. | 105/500 |
| 4,972,832 | 11/1990 | Traphi et al. | 128/402 |
| 5,016,029 | 5/1991 | Kanare | 128/402 |

FOREIGN PATENT DOCUMENTS

| 2548536 | 1/1985 | France | 128/402 |
|---|---|---|---|

*Primary Examiner*—Mark S. Graham
*Attorney, Agent, or Firm*—Jacobson & Johnson

[57] ABSTRACT

A resilient, body-conformable heat-retaining body pad for increasing the temperature of a selected portion of the body by retarding both the radiant heat loss and the conductive heat loss from the covered portion of the body. The resilient body conformable heat-retaining body pad includes a first sheet of flexible and inelastic material comprising a cloth-like flexible radiant heat-reflective material which is attached to one side of an elastic layer of thermal conductive insulation. The elastic layer of insulation retards the conductive heat losses from the covered portion of the body as well as provides conformability of the body pad to a user's body by permitting the body pad to be wrapped around a joint and still allow for joint movement of the covered porting of the body. Attached to the opposite side of the thermal conductive insulation layer is a stretchable-backing sheet which has an exterior surface of looped material which permits attachment of straps with multiple hooks, such as Velcro, to any portion of the exterior surface. The use of the loops on the exterior surface to permit a user to temporarily fasten the resilient body conformable heat-retaining body pad around a movable body joint with Velcro strips.

8 Claims, 2 Drawing Sheets

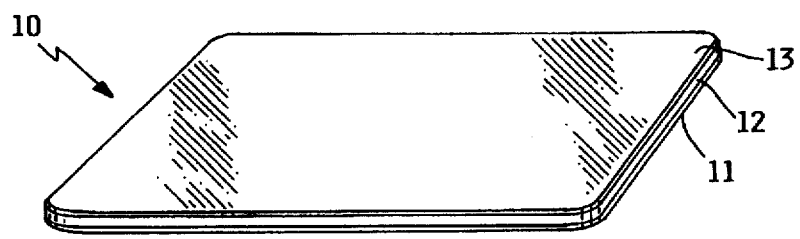
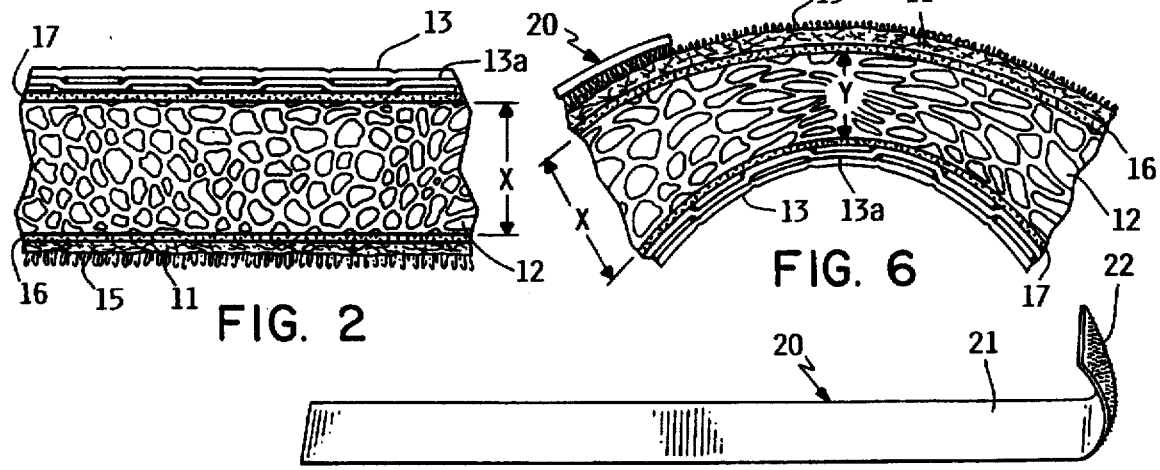
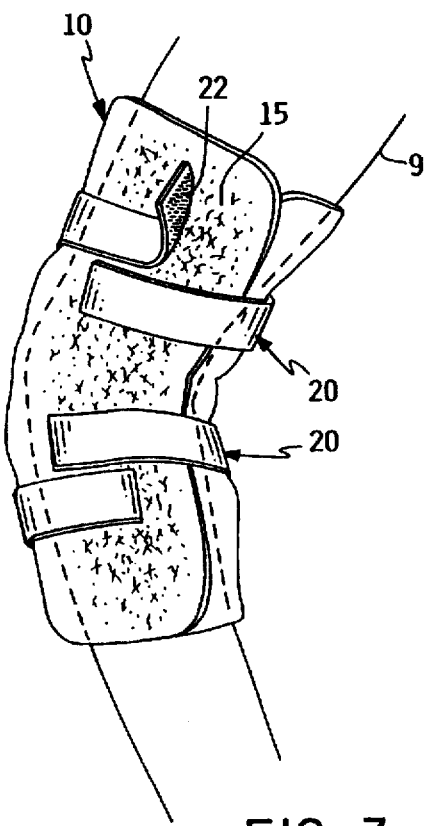
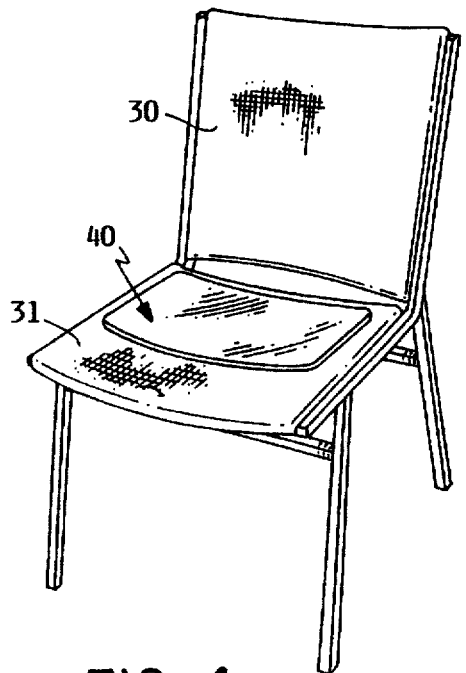

BODY PAD

This application is a continuation of application Ser. No. 07/702,502, filed May 20, 1991, now abandoned.

FIELD OF THE INVENTION

This invention relates generally to a heat-retention body pad and, more specifically, to a lightweight body-conformable heat-retention body pad that can be conformably and comfortably secured to various parts of the body to retard heat loss from the covered part of the body while permitting flexing of the covered body part. The elevation of the temperature of the body part can either be for comfort reasons or to ease the pain from an ailment.

BACKGROUND OF THE INVENTION

The concept of insulation for keeping body parts warm is well known in the art. Typically, insulating materials are incorporated into clothing to retard heat loss through the clothing. In some instances, radiant heat-reflecting materials are incorporated into body support devices so that the body can obtain both support and retain heat. In other instances, heat-reflecting materials are used as clothing or blankets.

One of the difficulties of the prior art body heat-retention devices is their bulkiness and lack of suitability for use on more than one part of the body. A further disadvantage is that the prior art radiant heat-reflecting materials, although flexible, are substantially inelastic and lack conformability to the body, particularly to joint areas of the body. If the devices do not conform to the body, the body loses heat through convection and, consequently, the devices are inefficient in retaining heat to maintain the covered portion of the body at an elevated temperature.

One of the difficulties is that heat-reflective materials used to reflect body heat are substantially inelastic and are difficult to conformably wrap around a user's body part and permit flee movement of the body part. This is particularly true for a body part such as an elbow which the user needs to move about. Wrapping a sheet of inelastic heat-reflecting material around a body part can inhibit movement of the body part, or, if loosely wrapped, becomes ineffective in retarding heat loss from the covered area of the body.

The Gruber U.S. Pat. No. 4,470,417 shows a prior art low back orthosis device for providing support and retarding heat losses to a portion of a user's back. The Gruber back support device has a heat reflective liner made from a heat reflecting material such as mylar, a foam pad and a fabric coveting that are sewed together at the edges. The entire heat reflective liner is supported within the Gruber back support device. The heat reflective liner of Gruber includes a fabric coating that has an exterior surface for securing his entire heat reflective liner to an inelastic panel located on the interior of his back support garment. To use the Gruber back support device the Gruber back support device is wrapped around the user's back and attached in the front of the user by elastic panels. The heat reflective liner is positioned in the garment to be located over the back region that requires heat treatment. The Gruber support garment uses an inelastic backing to support his entire heat reflective liner. Gruber compressively holds his heat reflective liner in place on the back of the user. While the Gruber device is suitable for use on flat non mobile regions of the body such as the back the Gruber device is not suitable for use in covering movable joints areas such as knees or elbows since the Gruber heat reflective liner mounts on an inelastic backing to hold his heat reflective liner in place and thus prevent movement of his heat reflective liner on the users back. The restrictiveness of the Gruber back support device precludes the user of the Gruber back support device on joint areas of the body since his entire heat reflective liner requires a separate inelastic support panel. In contrast to the Gruber back support device which uses an inelastic support for his entire heat reflective liner the present invention resiliently holds the body pad in place through the coaction of a stretchable-backing sheet and an elastic layer with only portions of the body stretchable-backing sheet engaging a strap to hold the body pad on a user's body.

The present invention solves the problem of attaching a heat retaining body pad over a movable joint of a user by providing a body conformable body pad that includes a layer of elastic material that is fastened coextensively to a stretchable-backing layer and to an inelastic but flexible heat-reflecting layer so that when the composite layer is wrapped around a user's joint such as an elbow and held in place by straps fastened to portions of the stretchable-backing material the coaction of the materials provides both a cushion and conformability to the body pad to allow the inelastic heat-reflecting material to shift and move as the user flexes his or her joint. The shifting movement permitted by the elastic layer also prevent the inelastic material from causing sore spots on the user's body as a result of contact with the inelastic layer.

The present invention provides an improved body conformable heat-retention body pad which has sufficient flexibility so that it can be comfortably and dynamically conformable around a body joint while still retarding both conductive and radiant heat losses. The body pad comprises a composite of materials that not only retards conductive and radiant heat losses but retains sufficient resiliency, so that when removed, it returns to a flat condition, allowing use of the body pad as a seat cushion to keep a user's posterior region protected from metal or concrete seam found at outdoor sporting events or the like. The flexibility of the present invention also enables a user to carry the body pad with him or her to permit the user to quickly place the pad on the body part which needs to retard heat loses.

DESCRIPTION OF THE PRIOR ART

U.S. Pat. No. 4,645,498 shows a body compress which has a bladder that can be filled with ice or hot water and is merely strapped around the body through the use of Velcro straps which are mounted directly to the device.

U.S. Pat. No. 4,081,150 shows a multi-purpose therapeutic pad which can be used to apply hot or cold to the device which is adjustable. It includes a pouch for receiving an electric heating pad or the like.

U.S. Pat. No. 3,815,610 shows a steam pack, having a contoured shape to wrap around the user's neck with a pocket for receiving a steam pack and placing adjacent to the user's neck.

U.S. Pat. No. 4,446,055 shows a bandage for applying cold to the body, with straps adapted to hold the compress to the user's body.

U.S. Pat. No. 4,587,962 shows a jacket-like device which fits around a patient's calf to provide support for an injured ankle.

BRIEF DESCRIPTION OF THE DRAWINGS

FIG. 1 is a perspective view of the invention;

FIG. 2 is an enlarged side view of the invention;

FIG. 3 shows the invention used as an elbow wrap;

FIG. 4 shows the invention in use as a seat cushion;

FIG. 5 shows a flexible fastening strap for use with my invention;

FIG. 6 shows the coaction of the layers in my body pad to resiliently cover a selective portion of the user's body;

BRIEF DESCRIPTION OF THE INVENTION

Figure 7:
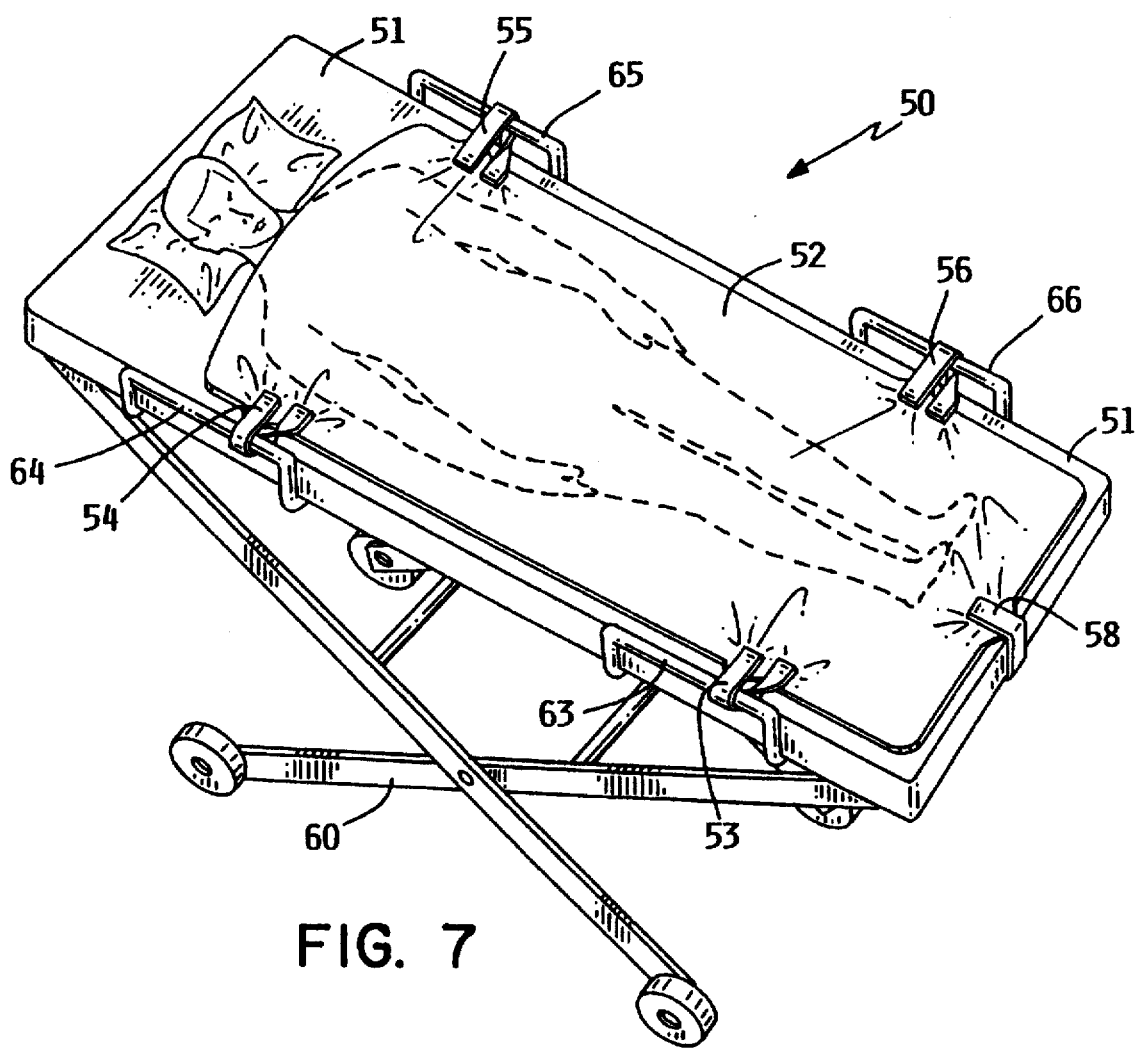
FIG. 7 shows my use of a body pad as a disposable blanket for a trauma victim.

Briefly, the invention comprises a resilient, body-conformable heat-retaining body pad for increasing the temperature of a selected portion of the body by retarding both the radiant heat loss and the conductive heat loss from the covered portion of the body. The resilient body conformable heat-retaining body pad includes a first sheet of flexible, substantially inelastic material comprising a cloth-like radiant heat-reflective material which is attached to one side of an elastic layer of thermal conductive insulation that retards the conductive heat losses from the covered portion of the body, as well as permits the body pad to be wrapped around a joint while allowing for joint movement. Attached to the opposite side of the thermal conductive insulation layer is a stretchable-backing sheet which has an exterior surface of looped material which permits attachment of straps with multiple hooks, such as Velcro, to any portion of the exterior surface. The use of the loops on the exterior surface permit a user to securely fasten my resilient body-conformable, heat-retaining body pad around a body joint with reusable Velcro ship fasteners. The invention has particular application for heat treatment of joints as well as use as a pad for humans or animals to sit on. One application of my invention is as use as an operating pad for veterinarians. The advantage of the pad is that it keeps the animal warm during surgery and that after surgery the pad can be disposed of. The use of an inelastic material which is vapor retardant permits the pad to not only retain body heat but to also retain body moisture so that a moist heat is provided to the user. In one embodiment the unit is formed in the shape of a pouch so that the pad can be placed around a portion of a users.'s body.

DESCRIPTION OF THE PREFERRED EMBODIMENT

FIG. 1, reference numeral 10, generally identifies my resilient body conformable heat-retaining body pad comprising three layers of material that are sandwiched together to produce a unitary body pad that is effective in comfortably conforming to the contours of the body to elevate the temperature of the portion of the body covered by the body pad without excessive convective loss of body heat from between the body pad and the user's body.

The body pad 10 comprises a first layer consisting of a stretchable-backing material 11 having an exterior surface 15 with multiple small loops for engaging with hook-type material such as Velcro straps. Typically stretchable-backing material 11 can be a loose woven cloth or other material that stretches when pulled on. The stretchability can be due to the distortability of the material or the weave used in the material. An example of a stretchable material is a knit fabric or the like. The loop-type material extends completely across the surface of the stretchable-backing material to permit attachment to Velcro straps anywhere on surface 15.

The stretchable-backing material is typically a cloth fabric which is flexible to conform to a body part.

Located proximate and secured to stretchable-backing material 11 is an intermediate core layer 12 comprising a thermally-insulating material that retards conductive transfer of heat therethrough. Insulation layer 12 comprises a resilient and elastic materiel that is attached coextensive with stretchable-backing material 11. Typically, insulation layer 12 comprises a layer of one-quarter inch thick, closed cell polyethylene foam. Depending on the application the insulation may be thicker to prevent conductive loss of heat. For example a layer three or four inches thick could be used in blanket applications. The thickness of the foam provides a cushion to the body part in contact with my body pad. The elastic of the insulation layer 12 allows the relative inelastic layer 13 to shift and move in response to movement of the user's body. The air pockets in the foam provide a conductive heat-insulation layer. The conductive insulating qualifies retard conductive heat loss therethrough.

Located on the top surface of body pad 10 and secured coextensively with insulation layer 12 is a sheet of flexible heat-reflecting material 13 comprising a flexible cloth-like material that is relatively inelastic. The heat-reflecting material is commercially available. One such heat-reflecting material is sold under the name FABRAFOIL The heat-reflecting material comprises a foil fabric hybrid where the foil is imbedded into the fabric and is virtually wrapped around the yarn. The FABRAFOIL material has a heat-reflective rating of approximately 85 percent of the heat and is as flexible as conventional fabrics. However, the inelasticity of the heat-reflecting material inhibits the movement of joint areas of the body. That is, wrapping and securing the inelastic material around a body joint inhibits it from moving. With the present invention, the inelastic material is allowed to float and move over the joint area since the elastic layer 12 and stretchable-backing material 11 resiliently holds the inelastic layer in place to provide the required degree of freedom. A further feature of the material is that the material is vapor impermeable so that the moisture given off by the body remains trapped beneath the body pad. Consequently, the user can obtain a moist heating effect from the bodies own heat mechanisms.

While each of the materials has its own characteristics, the coaction of the three different materials in a unitary-like construction provides a resilient yet flexible body pad that can be wrapped around a body joint and secured comfortably thereto while permitting flexing of the covered joint. A further advantage of the invention is that the body pad can be made of low cost materials so that the pad can be disposed of if the pad becomes contaminated.

FIG. 2 shows an enlarged side view of the present invention that illustrates the multiple layers that are sandwiched together. The stretchable-backing material 11 has an exterior surface with closely spaced loops 15 extending from it for attaching Velcro straps thereto. A layer of flexible adhesive 16 secures stretchable-backing layer 11 to core material 12 so that both stretchable-backing material 11 and core material 12 are held in coextensive secured relationship to each other. Similarly, a second layer of flexible adhesive 17 secures the opposite side of core material 12 to heat-reflecting material 13 so that both stretchable-backing material 11 and heat-reflecting material 13 are held in coextensive secured relationship to core material 12.

The sandwiching of the compressive flexible elastic core between the stretchable-backing layer and the heat-reflective material produces a body pad that is body conformable, resilient, heat retardant and cushioning. That is, the sandwiching of the relative inelastic material of the heat-reflecting material to the more elastic foam layer and the stretchable-backing material allows the body pad to flex and conform around a body part without binding or restricting the use of the covered joint. In addition, the combination produces a resiliency that allows the body pad to return to its original shape when removed form the body part. That is, with pressure removed, the more elastic layers and the stretchable-backing material provide a restoring force to pull the body pad back to its original shape.

A further feature of the sandwiching of the materials is that the heat-reflective cushion behind cushion behind the material to prevent the heat-reflective material from creating pressure a spot that unduly robs on the user's skin to create a sore.

FIG. 3 shows my body pad 10 wrapped around a person's elbow with loopside 15 facing outward; a first strap 20, having a smooth surface 21 on one side and a series of hooks 22 on the other side wrapped around one side of the joint and a second strap 23 also having a smooth side and a side with hook-like members wrapped around the other section of the joint to hold body pad 10 in place on the elbow.

FIG. 4, reference numeral 30, identifies a chair with pad 10 located thereon. In the use in FIG. 10, the straps are removed from body pad 10 and the body pad can be used as a seat cushion to keep the posterior of a person warm.

FIG. 5 shows an elongated Velcro strap 20 having hooks 22 to engage the loops on layer 11 to thereby permit fastening my body pad to a portion of a user's body.

To appreciate the unique conformability of the body pad produced by the present invention, refer to FIG. 6 which shows a portion of body pad 10 in a bent position. The relatively inelastic heat-reflecting layer 13 is located on the inside of the curve, and in normal use, would be the surface closest to the user's skin. Note the elastic layer 12 has a conventional thickness at the end which is denoted by x. When the body pad is wrapped around a portion of the body, the elastic material may compress at high points on the body as indicated by the shortened thickness dimension y.

Located on stretchable-backing material 11 is strap 20 that holds body pad 10 around a user's body. FIG. 6 shows that strap 20 does not directly attach to the inelastic heat-reflecting layer 13, but indirectly attaches to inelastic heat-reflecting layer 13 through cover or stretchable-backing layer 11 and elastic layer 12. The indirect fastening of inelastic heat-reflecting layer 13 through elastic layer 12 and stretchable-backing material 11 produces a resilient suspension of the inelastic heat-reflecting layer 13. As a result of the resilient suspension, inelastic heat-reflecting layer 13 can move with respect to fastening strap 20 to permit the body pad to conform to the movement of the user's body. That is, if the user bends his or her elbow, the layer of inelastic material 11 can shift and move about with respect to strap 20 and the body, since the layer of inelastic material is resiliently held proximate to the user's body by the coaction of the layer of elastic material 12 and the stretchable-backing material 11. Thus, the present invention permits wrapping a joint with an inelastic heat-reflecting layer to retard heat loses yet still allow the user to flex and move the joint about since the elastic materiel 12 and the stretchable-backing material 11 coact with straps fastened to only portions of the stretchable-backing material 11 to resiliently hold the inelastic material proximate the body joint of the user to permit flexing and bending of the joint while still retarding heat loss from the covered portion of the body.

Referring to FIG. 7 reference numeral 50 identifies a patient located on a stretcher 50. The stretcher includes a mattress 51 supported by a scissor like frame 60. Located on one side of stretcher 50 are handles or rails 63 and 64. Located on the other side are handles or rails 65 and 66. An injured patient is shown laying on mattress 51 with the patient covered by my disposable heat retaining blanket 52. One end of blanket 52 is held in place by Velcro strap 55 and Velcro strap 54 that are wrapped around their respective handles. Similarly the other end of blanket 52 is held in place by three Velcro straps 53, 56 and 58. Velcro straps are identical to the straps shown in FIG. 5. The Velcro strap 58 extends beyond the end of mattress 51 and fastens to the underside of the mattress to resiliently hold the body pad blanket on the patient.

The use of my body pad as a disposable blanket is particular use full with trauma patients that require keeping the person warm. The use of my disposable blanket body pad 52 is partially useful in instances where a person is bleeding. If a person bleeds on clothing or other garments used in handling the person the clothing must be destroyed. Consequently, coverings such as blankets must aim be thrown away. The present invention provides a low cost disposable body blanket that retains body heat to keep the person warm while at the same time providing a lightweight coveting for the patient.

Figure 8:
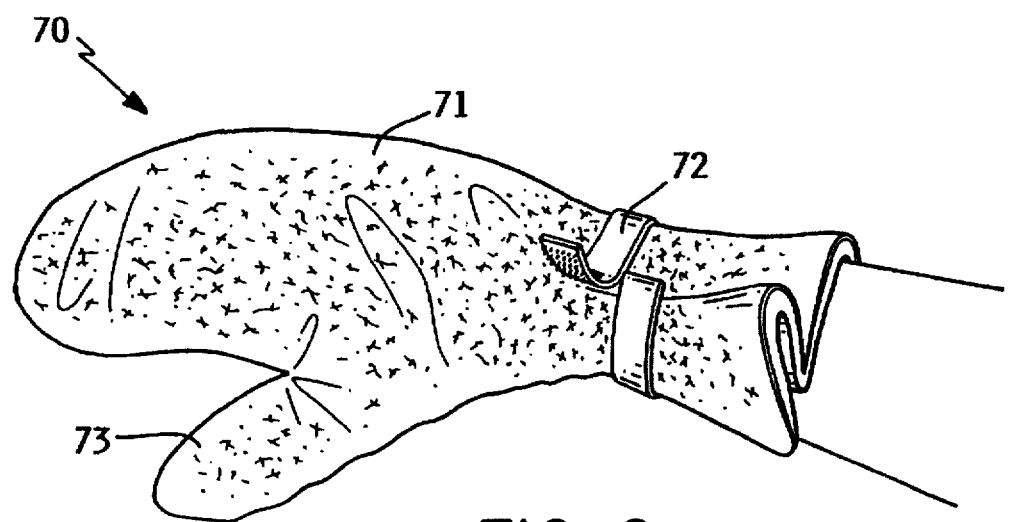
FIG. 8 shows a specialized use of my body pad which is formed in the shape of a pouch or bag to be secured around a portion of the user's body.

FIG. 8 shows my body pad made into the form of a pouch 70 to permit the pouch to placed around and sealed to a user's body. Pouch 70 includes a main portion 71 for a users hand and a second portion 73 for a user's thumb. A Velcro strap 72 identical to strap 20 is used to wrap around the body part to hold the pouch in position on the users hand. While use of my pouch is shown with a hand the pouch could also be used with a leg or in some instances a pouch for the user's body.

I claim:

1. A resilient body conformable unitary heat-retention apparatus for increasing the temperature of a selected portion of a body by retarding radiant heat loss and conduction heat loss from a selected portion of a body comprising:

a first sheet of flexible, inelastic, radiant heat-reflecting material, said sheet of flexible, inelastic, radiant heat-reflecting material having a radiant heat-reflective rating in excess of 85 percent;

a second sheet of flexible elastic material having a first side and a second side, said second sheet of flexible elastic material comprising a heat-conduction retardant material to retard the flow of heat from a selected portion of a body, said second sheet of flexible elastic material having the first side secured to said first sheet of flexible inelastic radiant, heat-reflecting material;

a stretchable-backing sheet, said stretchable-backing sheet having an exterior surface comprised of loop members to permit attachment of hooked members thereto, said stretchable-backing sheet having a second side, said second side of said stretchable-backing sheet secured to said second side of said flexible elastic material so that said second sheet of flexible elastic material and said stretchable-backing sheet have regions substantially coextensive with each other, to provide a unitary flexible heat-retention apparatus, said first sheet of flexible, inelastic, radiant heat-reflecting material, said second sheet of flexible elastic material and said flexible elastic material stretchable-backing sheet coacting with each other to provide a resiliency to said body pad to cause said body pad to return to its original shape when said body pad is deformed or bent; and an elongated flexible strap having a first end, a second end and an intermediate region with hook members located on said first end of said strap and on said second end of said strap to permit temporary attachment of the first end of said strap to a first portion of said loop members so that a user can wrap the unitary heat-retention apparatus around a selected portion of a body and thereby secure the unitary heat-retention apparatus on a selected portion of a body by attaching the other end of said strap to a further portion of said loop members to thereby hold the heat-retention apparatus around a selected portion of a body in a condition that allows the unitary heat-retention apparatus to flex and move as the user moves about, so that body heat generated from a selected portion of a body covered by said unitary heat-retention apparatus is retarded from both radiant heat loss and conductive heat loss to thereby raise the temperature of a selected portion of a body located proximate to and covered by said first sheet of flexible inelastic, radiant heat-reflecting material.

2. The body pad of claim 1 wherein said inelastic material comprises an insulating material.

3. The body pad of claim 1 wherein said elastic material comprises polyethylene foam.

4. A resilient, unitary body pad for comfortably conforming to a user's body comprising:

a first layer of flexible and relative inelastic heat-reflecting material of a first thickness for placing proximate a user's body to retard the loss of radiant heat from a portion of the user's body located proximate the flexible and relative inelastic heat-reflecting material, said flexible and relative inelastic heat-reflecting material having a first surface free of any covering, said flexible and relative inelastic heat-reflecting material having a second surface located opposite said first surface;

a second layer of an elastic compressible material, said layer of elastic compressible material having a a thickness greater than said first thickness of said flexible and relative inelastic heat-reflecting material, said layer of elastic compressible material having a first surface and a second surface;

a first adhesive, said first adhesive securing said second surface of said layer of flexible and relative inelastic heat-reflecting material to said first surface of said layer of elastic compressible material to permit localized expansion or compression of said layer of elastic compressible material in response to localized flexing of said layer of flexible and relative inelastic heat-reflecting material;

a third layer of a stretchable backing material, said layer of stretchable backing material having a first surface on one side of said stretchable material and a second surface on an opposite side of said layer of stretchable material; and a second adhesive for securing said first surface of said layer of stretchable material to said second surface of said elastic compressible material to provide a unitary coactive construction between said layer of elastic compressible material and said layer of stretchable material, said unitary co-active construction consisting of said first layer, said second layer and said third layer coextensively sandwiched together with said second layer of an elastic compressible material located between said first layer of flexible and relative inelastic material and said third layer of stretchable backing material with said layer of flexible and relative inelastic heat-reflecting material and said layer of stretchable material coacting with each other through said layer of an elastic compressible material to provide a coactive resiliency to allows said body pad to conform to a portion of a user's body while simultaneously urging said body pad to return to its original shape with said layer of elastic compressible material providing a resilient buffer between said layer of flexible and relative inelastic heat-reflecting material and said stretchable backing material to permit said layer of flexible and relative inelastic heat-reflecting material to flex and move as a single layer in response to the movement of the portion of a body covered by said flexible and relative inelastic heat-reflecting material while retarding the loss of heat from a user's body to thereby elevate the temperature of a user's body covered by said flexible and relative inelastic heat-reflecting material.

5. The body pad of claim 4 wherein said elastic material is approximately ¼ inch thick.

6. The body pad of claim 4 wherein said elastic material is held proximate said inelastic material with a layer of flexible adhesive.

7. The body pad of claim 6 wherein said body pad has a rectangular shape sufficiently large to permit wrapping around a portion of a user's body.

8. The body pad of claim 7 wherein said first surface having spaced regions (15) for fastening a strap thereto including two elongated straps (20) having hooks (22) thereon to engage the spaced apart regions (15) on said body pad to thereby permit a body pad to be secured to a user's body, said straps spaced apart to permit securing of one of said straps to one of the spaced apart regions (15) on one side of a movable body joint and the other strap to the other spaced apart region (15) on the other side of the movable body joint to permit the straps to hold the body pad around the body joint even though the body joint is flexed and moved with respect to the body pad.

* * * * *